United States Patent
Neubeck

(10) Patent No.: US 11,953,497 B2
(45) Date of Patent: *Apr. 9, 2024

(54) BREATH SENSING DEVICE FOR A PORTABLE ELECTRONIC DEVICE

(71) Applicant: BOYDSENSE, INC., South San Francisco, CA (US)

(72) Inventor: Kurt Neubeck, Miltenberg (DE)

(73) Assignee: BOYDSENSE, INC., San Bruno, CA (US)

(*) Notice: Subject to any disclaimer, the term of this patent is extended or adjusted under 35 U.S.C. 154(b) by 801 days.

This patent is subject to a terminal disclaimer.

(21) Appl. No.: 16/627,657

(22) PCT Filed: Jul. 2, 2018

(86) PCT No.: PCT/US2018/040547
§ 371 (c)(1),
(2) Date: Dec. 30, 2019

(87) PCT Pub. No.: WO2019/010110
PCT Pub. Date: Jan. 10, 2019

(65) Prior Publication Data
US 2021/0156843 A1 May 27, 2021

(30) Foreign Application Priority Data
Jul. 4, 2017 (EP) ..................................... 17179646

(51) Int. Cl.
*G01N 33/497* (2006.01)
*A61B 5/091* (2006.01)

(52) U.S. Cl.
CPC .......... *G01N 33/497* (2013.01); *A61B 5/091* (2013.01); *A61B 2560/0431* (2013.01); *A61B 2562/0204* (2013.01)

(58) Field of Classification Search
CPC .......... G01N 33/497; A61B 2562/0204; A61B 2560/0431
See application file for complete search history.

(56) References Cited

U.S. PATENT DOCUMENTS

2011/0009764 A1* 1/2011 Lanier .................... A61B 5/417
600/532
2013/0344609 A1 12/2013 Mayer et al.
(Continued)

FOREIGN PATENT DOCUMENTS

CN 103512926 1/2014
CN 104237456 12/2014
(Continued)

OTHER PUBLICATIONS

Extended European Search Report dated Jan. 4, 2022 for European Patent Application No. 21181593.1.
(Continued)

*Primary Examiner* — Jamel E Williams
*Assistant Examiner* — Alex T Devito
(74) *Attorney, Agent, or Firm* — BARNES & THORNBURG LLP; Jeffrey R. Stone

(57) ABSTRACT

The invention relates to a breath sensing devices for a portable apparatus, in particular a portable telecommunication device or a wearable device, the sensing device comprising an acoustic wave sensing means, like a microphone; and a gas sensing means, The invention furthermore relates to an electronic device comprising such a sensing device. In addition, methods are provided that allow calibrating a gas volume based on an output signal of an acoustic wave sensing means.

9 Claims, 5 Drawing Sheets

(56) References Cited

U.S. PATENT DOCUMENTS

Figure 1:
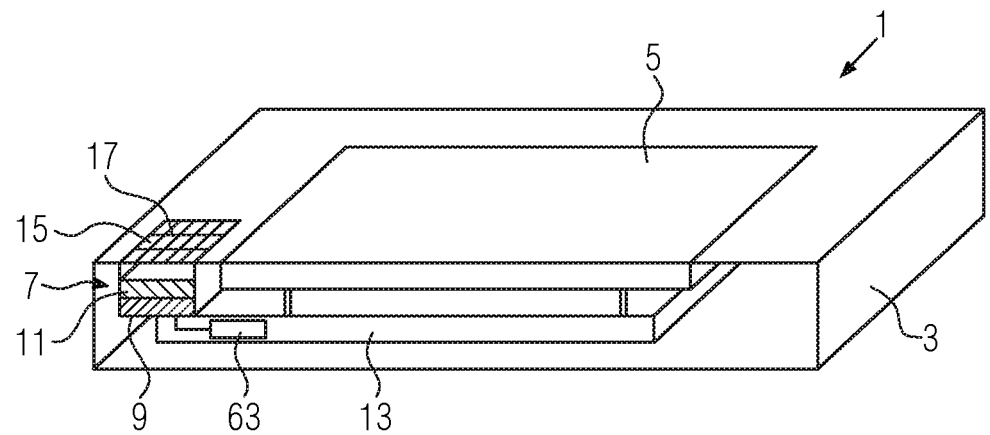

2015/0226585 A1    8/2015   Yang
2015/0355161 A1   12/2015   Takeuchi

FOREIGN PATENT DOCUMENTS

| | | | |
|---|---|---|---|
| EP | 2762880 | 8/2014 | |
| EP | 2762880 A1 * | 8/2014 | ......... G01N 33/4972 |
| EP | 2816352 B1 * | 12/2016 | ......... G01N 33/0059 |
| GB | 2534173 | 7/2016 | |
| WO | WO-2013191634 A1 * | 12/2013 | ............. A61B 5/082 |

OTHER PUBLICATIONS

Office Action dated Jun. 30, 2020 issued in related Chinese Patent Application No. 2018800425652.
International Search Report and Written Opinion issued in related PCT application No. PCT/US2018/040547, dated Sep. 18, 2018.

\* cited by examiner

BREATH SENSING DEVICE FOR A PORTABLE ELECTRONIC DEVICE

The invention relates to a breath sensing device for a portable electronic device. It furthermore relates to a portable device comprising such breath sensing device and to a method for estimating the volume of the sensed gas. The invention is of particular interest for a breath sensing device of a user to identify one or more particular molecules related to a disease.

Such breath sensing devices are known in the form of breath testers, e.g. to estimate the amount of alcohol consumed. The known devices are rather voluminous and have a high energy consumption. This makes it difficult to integrate them into portable electronic devices, like smart phones or in general wearables, to provide the user with gas sensing capabilities, e.g. for monitoring their environment or their health within the electronic device they use to communicate or work with on a regular basis.

In addition, those gas sensors are rather costly, which is in particular related to the gas volume determining functionality they have to satisfy. Indeed, to be able to obtain the concentration of a given molecule in the ambient air or the breath of the user, a calibration of the air volume to be analysed has to be carried out. In the case of breath testers, a precise calibration is necessary and achieved by using a rather voluminous and expensive mechanism with admission and exhaust pipes and a mechanical spring loaded switch, which allows the air flow to enter the analyzing chamber as long as the calibrated volume has not yet been achieved and then switches the piping system such that additional air is exhausted directly via the exhaust pipe without entering the measurement chamber.

Other approaches try to get rid of the mechanical parts of the volume calibration by trying to model the gas flow using software algorithms based on statistical data, the geometry of the device and/or the gas admission time. Up to now, these models did not provide sufficiently reliable results.

Furthermore, portable electronic devices with chemical sensors are for instance known from US 2014/0208829A1 or from US 2015/0226585A1.

It is an object of the present invention to provide a breath sensing device that overcomes the problems observed in the art. In particular, it is the object of the present invention to provide a breath sensing device that the establishment of a measure proportional to the gas volume of the breath of a user.

The object of the invention is achieved with a first breath sensing device for a portable electronic device according to claim 1. The inventive breath sensing device for a portable electronic device, in particular a portable telecommunication device or a wearable device, comprises: an acoustic wave sensing means, in particular a microphone, and a gas sensing means sensitive to at least one type molecules, and a first and second gas flow sensing means, wherein the acoustic wave sensing means, the gas sensing means and the first gas sensing means are arranged such that they are accessible to a gas flow, in particular the breath of a user, whereas the second gas flow sensing means is isolated from the gas flow. Using the second gas flow sensing means it is possible to discriminate flow contributions from a user's breath from a gas flow entering the device due to a movement of the device or due to the environment.

According to an embodiment, the breath sensing device can comprise more than one gas sensing means to be able to sense more than one type of molecule.

According to an embodiment the first and the second breath sensing means can be of the same type, in particular a thermistor or a humidity sensor or an anemometer, in particular a hot-wire anemometer. Using these sensors reliable flow data can be obtained and easy integration into a sensing device comprising an acoustic wave sensing means and a gas sensing means.

The object is also achieved with a second breath sensing device for a portable electronic device in particular a portable telecommunication device or a wearable device according to claim 3, The breath sensing device comprises: an acoustic wave sensing means, in particular a microphone, and a first gas sensing means sensitive to at least one type of molecule and a second gas sensing means sensitive to at least one other type of molecule, in particular $CO_2$ or a humidity sensor. Whereas the concentration of $CO_2$ in ambient air is of the order of 0.04 percent by volume, this percentage is of the order of 3.5 to 5 percent by volume in the exhaled gas. Using a second gas sensing means that is responsive to carbon dioxide, the important change in $CO_2$ concentration can be exploited to identify the time period during which a user is blowing into the breath sensing device. In case a humidity sensor is used, one also takes advantage of the presence of humidity of the exhaled gas of a user which is typically different than the one of the environment. Thus, the signal of the humidity sensor will see a change in humidity when a user breaths into the sensing device.

According to an embodiment, the breath sensing device can comprise further gas sensing means to be able to sense more than one type of molecule.

According to an embodiment, the acoustic wave sensing means can be provided over a substrate and the first and second gas sensing means are stacked over the acoustic wave sensing means, in particular the one over the other or the one besides the other one. Thus an integrated device needing only a small volume can be formed.

The object is also achieved with a third breath sensing device for a portable device, in particular a portable telecommunication device or a wearable device, according to claim 5. The third breath sensing device comprises: an acoustic wave sensing means, in particular a microphone with a membrane, a gas sensing means sensitive to at least one type of molecule, and further comprising a signal analyzing means configured to determine a DC electrical signal contribution to the total electrical signal received from the acoustic wave sensing means and configured to integrate the DC electrical signal over a predetermined time frame. The DC electrical signal contribution is a measure of the pressure applied onto the acoustic wave sensing means during a user's breath. By integrating that value over time one obtains a measure that is proportional to the gas volume of the breath.

According to an embodiment, the breath sensing device can comprise further gas sensing means to be able to sense more than one type of molecule.

According to an embodiment, the signal analyzing means can be furthermore configured to integrate the electrical signal received from the gas sensing means over the predetermined time frame and to determine the ratio of the integrated electrical signal received from the gas sensing means and the integrate DC electrical signal. The ratio between the two integrals is proportional to the concentration of the molecule of interest in the user's breath and can therefore be used to monitor the health condition of a user of the device.

According to an embodiment, the gas sensing means can be based on at least one of a metal oxide (MOX), in particular a tin oxide, carbon nanotubes (CNTs), a gold nanoparticle, a silicon nanowire, a quartz crystal microbalance (QCM), a colorimetric sensor, and a conductive polymer. These technologies provide reliable results and at the same time have a low energy consumption, in particular the nanotubes. Furthermore their fabrication can be integrated with the fabrication process of the acoustic wave sensing means and a common CMOS base can be used. Mox based gas sensing has the advantage of being non selective whereas other technologies like the carbon nanotubes are selective.

According to an embodiment, the gas sensing means can be arranged in or on or over a movable plate or in or on or over a fixed plate, of the acoustic wave sensing means. By providing the gas sensing means directly on one of the layers of the acoustic wave sensing means the design of the device can be simplified. In particular, according to a variant, a hot plate as part of the gas sensing means could be part of the movable plate or the fixed plate of the acoustic sensing means. This would further reduce the fabrication costs.

The object of the invention is furthermore achieved with a portable electronic device, in particular communication device, comprising a breath sensing device as described above.

According to an embodiment, the portable electronic device can further comprise a housing with a hole, wherein both the gas sensing means and the acoustic wave sensing means of the breath sensing device are positioned within and/or aligned with the same hole. Thus, without having to add an additional hole into the housing of the portable electronic device, it becomes possible to add a new functionality to the device, namely gas sensing to monitor the environment or to monitor some health indicators. Depending on the embodiment only the reference sensor needs to be positioned elsewhere.

The object of the invention is furthermore achieved with the method for sensing the breath of a human or an animal using the first breath sensing device. The method comprises the steps of integrating the difference of the signals received from the first and the second breath sensing means over a predetermined time frame to determine a signal proportional to the gas volume of the user's breath. With this embodiment gas flow contributions not originating from the user's breath can be removed from the signals, thereby improving the accuracy of the device.

According to an embodiment, the method can comprise a step of integrating the electric signal of the gas sensing means for the same predetermined time frame. By doing so, a measure proportional to the amount of molecules of interest in the gas flow of the breath from the user can be obtained.

The object of the invention is furthermore achieved with the method for sensing the breath of a human or an animal, using the third breath sensing device. The method comprises the steps of determining a DC electrical signal contribution to the total electrical signal received from the acoustic wave sensing means and integrating the DC electrical signal over a predetermined time frame to determine a signal proportional to the gas volume of the user's breath. The DC electrical signal contribution is a measure of the pressure applied onto the acoustic wave sensing means during a user's breath. By integrating that value over time one obtains a measure that is proportional to the gas volume of the breath.

According to an embodiment, the start of the time frame can be triggered by the point in time at which a difference between the signals of the first and second breath sensing means or the DC electrical signal contribution exceeds a predetermined threshold.

The object of the invention is furthermore achieved with the method for sensing the breath of a human or an animal, using the second breath sensing device. The method comprises the steps of starting integrating the signal received from the first gas sensing means over a predetermined time frame when the signal from the second gas sensing means or the humidity sensor exceeds a first threshold, and starting integrating the signal received from the second gas sensing means over the predetermined time frame when the signal from the second gas sensing means or the humidity sensor exceeds the first threshold to determine a signal proportional to the gas volume of the user's breath. The $CO_2$ content in the exhaled air and the humidity are parameters than can be directly attributed to the breath of the user, and therefore allow the determination of the gas flow with high accuracy.

According to an embodiment, the end of the time frame can be triggered by the subsequent point of time at which the difference of the signals or the signal from the second gas sensing means or the DC electrical signal contribution falls below a predetermined second threshold, in particular below the first threshold, or when the integral of the difference or the signal from the second gas sensing means or the integral of the DC signal contribution exceeds a third threshold.

Preferably, the method can further comprise a step of determining a ratio based on the signal received from the gas sensing means and the signal proportional to the gas volume and calibrating the ratio using a value representative for the ratio obtained by a different sensing method. In order to determine a proportionality factor between the ratio of interest, e.g. the concentration of a given molecule per volume, one can for instance use the known concentration of the given molecule or corresponding molecule, in the user's blood. Thus, at the moment a practitioner takes a blood sample, the user blows into the device and the ratio obtained from the gas sensing means to the signal proportional to the gas volume will correspond to the value of the molecule concentration in the blood of the user.

Additional features and advantages of the present invention will be described with reference to the drawings. In the description, reference is made to the accompanying figures that are meant to illustrate preferred embodiments of the invention. It is understood that such embodiments do not represent the full scope of the invention. The invention has been presented with respect to analyzing a user's breath, but instead or in addition the breath sensing device according to the invention could also be used to analyse the ambient air.

Figure 2:
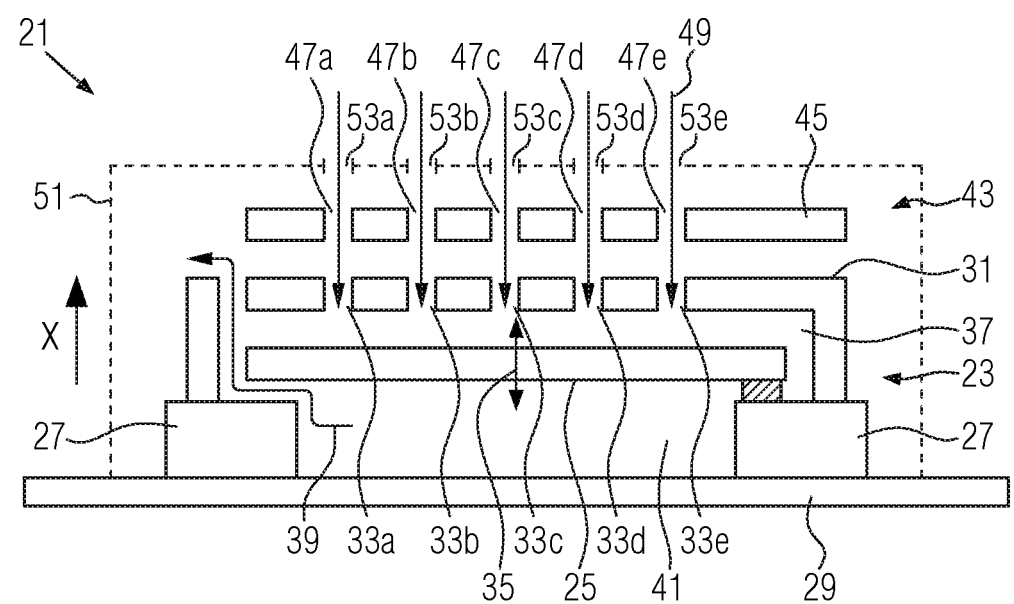
Figure 3:
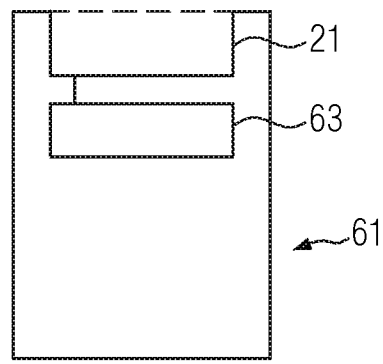
Figure 4:
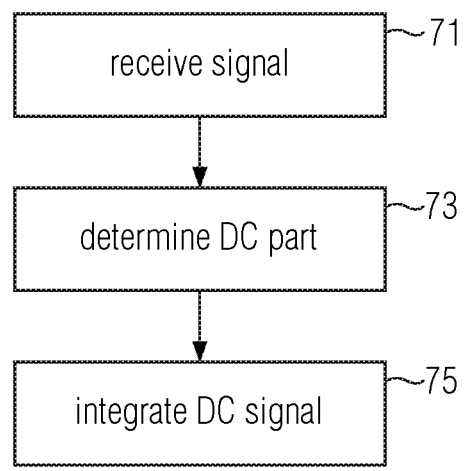
Figure 5:
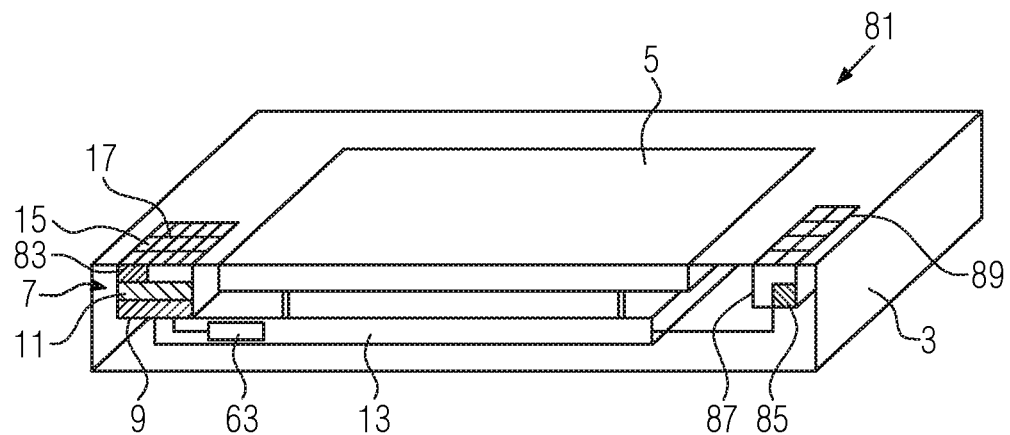
Figure 6:
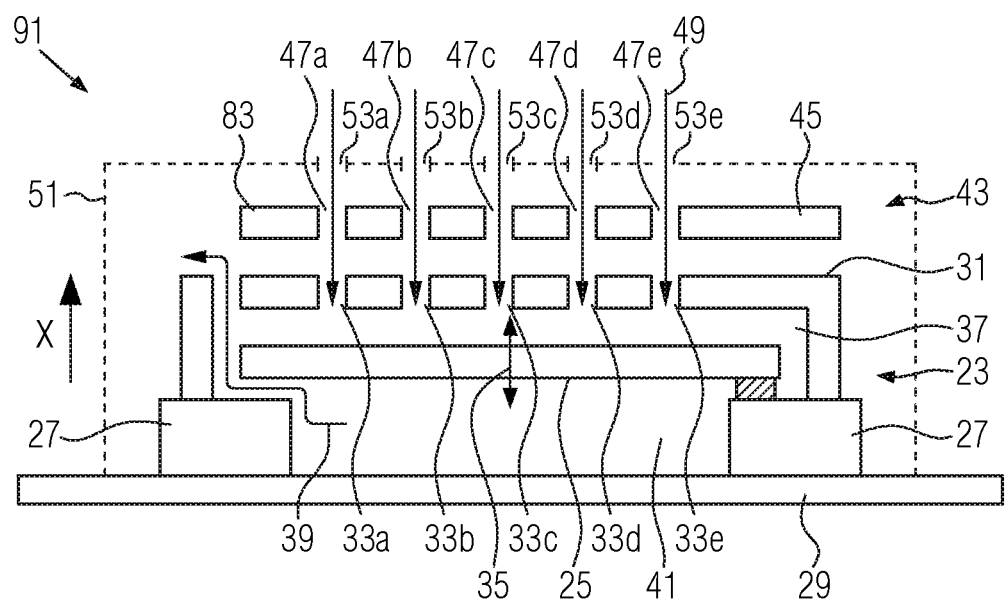
Figure 7:
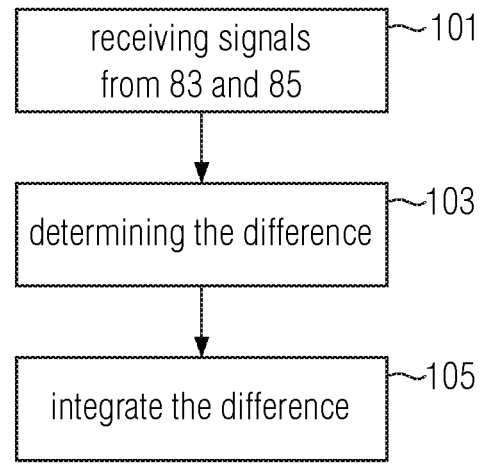
Figure 8:
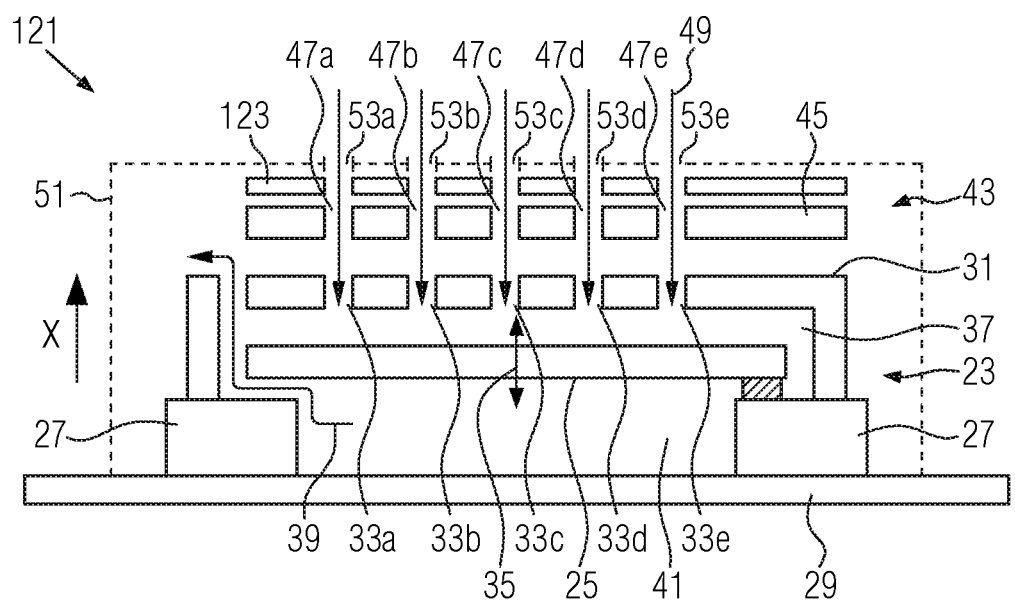
Figure 9:
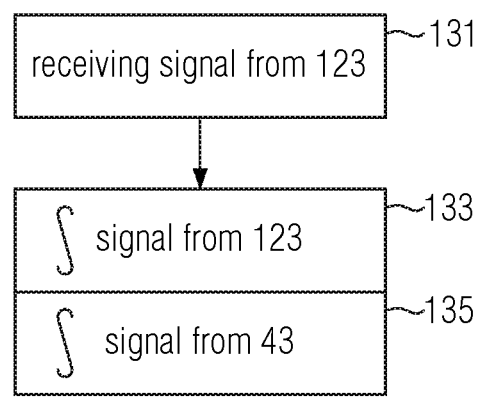

FIG. 1 illustrates an electronic device with a sensing device having features in common with all embodiments of the invention, FIG. 2 illustrates schematically the first embodiment of the breath sensing device according to the invention, FIG. 3 illustrates schematically the signal analyzing means of the breath sensing device according to the first embodiment, FIG. 4 illustrates a method to determine a measure proportional to the volume of gas of a user's breath, FIG. 5 illustrates an electronic device with a breath sensing device according to the second embodiment of the invention, FIG. 6 illustrates schematically a part of the second embodiment of the breath sensing device according to the invention, FIG. 7 illustrates a method to determine a measure proportional to the volume of gas of a user's breath according to the second embodiment, FIG. 8 illustrates schematically the third embodiment of the breath sensing device according to the invention, FIG. 9 illustrates a method to determine a measure proportional to the volume of gas of a user's breath according to the third embodiment.

FIG. 1 illustrates schematically a cut through an electronic device 1 with features in common for all embodiments of the invention that will be described further down with respect to the other figures.

The electronic device, here in particular a mobile communication device, comprises a housing 3, a display device 5 and a breath sensing device 7 with an acoustic wave sensing means, here a microphone 9, and a gas sensing means 11 sensitive to at least one type of molecule, connected to a motherboard 13 comprising the various electronic components and electrical interconnections as well as input/output means (not shown) for data processing of the electronic device 1. The motherboard 13 comprises a signal analyzing means 63 for treating the signals from the breath sensing device 7. Instead of using one gas sensing means 11, the breath sensing device can also comprise further gas sensing means to be able to sense more than one type of molecule.

The breath sensing device 7 is placed into an opening or a hole 15 present in the housing 3. Here, the opening 15 is covered by a grid 17, protecting the breath sensing device 7 against dirt, like dust particles. The breath sensing device 7 could also be positioned such that it is underneath the hole 15 in the housing 3 but aligned with it.

The electronic device 1 can be a mobile phone, a smart phone, a tablet, a laptop, a personal electronic assistant, a tracking device, an electronic wrist watch, an electronic wearable or the like.

According to the invention, the breath sensing device 7 combines the functionality of a microphone 7 enabling acoustic inputs to the electronic device 1, and stacked thereon the gas sensing means 11 for analyzing gases that enter the breath sensing device 7 into one sensor. The gas sensing means 11 is configured to analyse a user's breath, e.g. to carry out a breath test or to identify certain molecules indicative of a disease. Without departing from the invention, the breath sensing device 7 could also be configured to analyse the ambient air, e.g. to check the air quality as an alternative or in addition to analyzing the user's breath.

By stacking the gas sensing means 11 onto the microphone and thereby combining two functionalities that base their output signals on physical and/or chemical properties of a gas entering the sensing device 7, it becomes possible to use just one and the same hole 15 in the housing 3. This keeps the design of the housing 3 and the electronic device 1 simple and cost effective.

FIG. 2 illustrates an enlarged view of a sensing device 21 according to the first embodiment of the invention as defined in the claims 5 to 8. The sensing device 21 could for instance be used as sensing device 7 in the electronic device shown in FIG. 1.

The sensing device 21 comprises an acoustic wave sensing means, here a microphone 23. The microphone 23 in this embodiment is a MEMS microphone readily used in mobile phones, like smart phones. A MEMS microphone is an acoustic transducer transforming acoustic signals into electrical signals. The microphone 23 comprises a movable plate 25 arranged on a pillar structure 27a, 27b over a substrate 29. The pillar structure can also be obtained by providing a cavity inside the substrate 29. The microphone 23 further more comprises a stiff plate 31, also called back plate or fixed plate, arranged over and at a distance of the movable plate 27. The stiff plate 31 comprises holes 33a-33e.

The movable plate 27 and the stiff plate 31 form a capacitor, and changes in the capacity due to the acoustic vibrations are translated into capacity changes which lead to the electrical signals at the output of the microphone 23.

The capacitive change is caused by the acoustic waves of the sound passing through the holes 33a to 33e. The movable plate 25 flexes in response to the change in air pressure caused by the acoustic waves as indicated by the double arrow 35. The movable plate 25 thus acts like a membrane. The movement will modulate the gap 37 between the movable plate 25 and the stiff plate 31 which in turn also modulates the capacity between the two plates. The air in the chamber 41 formed between the substrate 29, the pillar structure 27a, 27b and the movable plate 25 flows out and back in via a ventilation path 39. The chamber 41 thus forms a kind of acoustic resonator which is linked to the outside of the sensing device 21 via the ventilation path 39.

The sensing device 21 furthermore comprises a gas sensing means 43 arranged over, in particular, on the microphone 23.

It comprises a gas sensitive layer 45 with a plurality of perforations 47a to 47e. In this embodiment, the perforations 47a to 47e are aligned with the perforations 33a to 33e of the microphone 23 along the thickness direction X of the sensing device 21. By doing so, the air or gas entering the sensing device 21, e.g. the breath of a user when the user talks or breaths into the electronic device, can reach the microphone 23. At the same time, the air or gas can be analysed using the same flow.

In this embodiment, the gas sensitive layer 45 is a metal oxide based sensing device. The detection principle is based on a change of the resistance of a thin film upon adsorption of the gas molecules on the surface of a semiconductor. One example of a metal oxide is tin oxide. According to variants of the invention, the gas sensing means 43 can comprise carbon nanotubes (CNTs), gold nanoparticles, a silicon nanowire, a quartz crystal microbalance (QCM), a colorimetric sensor, and a conductive polymer. Theses technologies have the advantage of low energy consumption. Selective and non selective technologies can be chosen and/or combined.

According to a variant of this embodiment, a common housing 51, illustrated in dashed lines in FIG. 2, can be used to package the microphone 23 and the gas sensing means 43 together into one device. The housing 51, preferably, has perforations 53a to 53 aligned with the perforations of the microphone 23 and the gas sensing means 43.

The breath sensing device 21 can be part of an array of devices or a stack.

The breath sensing device 21 furthermore comprises a signal analyzing means, either integrated into the breath sensing device 21 or is part of the electronic components of the electronic device 1.

FIG. 3 illustrates schematically the electronic device 61 with the breath sensing device 21 and the signal analyzing means 63. The signal analyzing means 63 is configured to establish a measure that is representative of the volume of gas to determine a ratio of the molecules the presence of which is attributed to a certain disease to the gas volume. The method to obtain the measure representative of the volume of gas is illustrated in FIG. 4.

In Step 71, the signal analyzing means 63 receives the signals from the microphone 23 and the gas sensing means 43. The signals received are analog or digital and can already be treated by applying filters etc.

In Step 73, the signal analyzing means 63 determines a DC (direct current) electric signal contribution out of the electrical signal received from the acoustic wave sensing means, thus here the microphone 23.

When a user blows into the hole 15, the gas flow impinging on the movable plate 25 will push the plate 25 and thereby change the capacitance. However, compared to the acoustic waves while talking into the microphone, the signal created by the gas flow when blowing into the microphone will lead to a static signal which translates into the DC signal contribution $X_{DC}$. Therefore the DC signal is a measure of the pressure.

Furthermore, as illustrated in Step 75, by integrating the DC contribution over the duration of the breath, one gets a measure that is proportional to the gas volume V that passed through the breath sensing device 21.

$$V \propto \int_{t0}^{t1} X_{DC}(t)dt, \quad \text{(formula 1)}$$

with $t_0$ corresponding to the beginning of the breath and $t_1$ corresponding to the end of the breath.

When breathing onto the breath sensing device 21, the gas sensing means 43 will capture the type of molecule one is interested in to determine the health condition of the user and a signal Y(t) is obtained that is a measure for the amount of molecules that impinge at the moment t on the gas sensing means 43. By integrating Y(t) over the duration of the breath, thus from $t_0$ to $t_1$ like in formula 1, one obtains a measure proportional the amount of molecules S in the breath.

$$S \propto \int_{t0}^{t1} Y(t)dt \quad \text{(formula 2)}$$

The ratio of the two integrals is thus proportional to the amount of molecules of interest over the volume of the gas flow which would be a measure for the health condition.

To obtain the proportionality factor α, the system has to be calibrated. One way to obtain the factor α is to correlate the breath measurement with other types of measurements. For instance, the concentration P of the molecule of interest in the blood could be determined by a practitioner. At the time of taking the blood, the user blows into the breath sensing device 21 so that the two integrals in formula 1 and 2 can be determined under the same health condition. The value P is linked to the breath measurement by a proportionality factor α which can thus be determined based on P and the two integrals.

$$P = \alpha \cdot \frac{\int_{t0}^{t1} Y(t)dt}{\int_{t0}^{t1} X_{DC}(t)dt} \text{ so that } \alpha = P \cdot \frac{\int_{t0}^{t1} X_{DC}(t)dt}{\int_{t0}^{t1} Y(t)dt} \quad \text{(formula 3)}$$

Having established the proportionality factor, it then becomes possible to follow the evolution of the concentration of the molecule in the breath of a user. The user will be able to identify fluctuations in $P_{sensed}$ so that he can seek medical advice promptly.

In this embodiment, the beginning $t_0$ of the breath is the moment at which the DC electrical signal contribution exceeds a predetermined first threshold. The end $t_1$ of the breath can be triggered by the subsequent point in time at which the DC electric signal contribution falls below a second threshold, in particular the first threshold. According to a variant the end of the time frame could also the moment at which the integral of the DC electrical signal contribution exceeds a third threshold.

FIG. 5 illustrates schematically a cut through the electronic device 81 according to the second embodiment, in particular in relation to claims 1 and 2. Features with reference numerals already used in the description of the FIGS. 1 to 4 will not be described again but reference is made to their description above.

In addition to the features as already illustrated in FIG. 1, the second embodiment further comprises a first and second breath sensing means 83 and 85. The first breath sensing means 83 is arranged in the vicinity of the gas sensing means 11. The second breath sensing means 85 is arranged away from the first breath sensing means so that it is isolated from the gas flow of the breath of a user. Thus, in use the second breath sensing means 85 is not sensing the breath of the user, but only measures the gas flow of the environment. In this embodiment the second breath sensing means is arranged in a second hole 87 of the housing 3 which can also be covered by a grid 89. The second hole in the housing 3 could for example be the one to place the speaker of the electronic device 81.

FIG. 6 illustrates a part of the breath sensing device 91 used in the second embodiment. In addition to the elements already described with respect to the breath sensing device 21 of FIG. 2, the breath sensing device 91 comprises the first breath sensing means 83.

The first and second breath sensing means 83 and 85 are, in this embodiment, of the same kind and can for instance be one of a thermistor, a humidity sensor or an anemometer, in particular a hot-wire anemometer and allow measuring flow of a gas instead of pressure like in the first embodiment. Thus, the breath sensing means could also be qualified as gas flow sensing means. As the signal of the second breath sensing means 85 is isolated from the user's breath, the difference between the two signals received can be attributed to the user's breath, so that any flow resulting from the movement of the device or a flow present in the environment can be cancelled out of the signal. Thus, like in the first embodiment, integration over time of the difference between the two signals in a signal analyzing means will also give a measure of the gas volume of the user's breath.

When using a thermistor, like a NTC resistor, one measures temperature and as soon as a temperature difference between the first and second breath sensing means 83 and 85 is observed, one detects the presence of breath. Thus one takes advantage of the temperature difference between the breath and the environment to detect the flow which translates in a resistance change in the thermistor.

When using an anemometer, a heated resistor is used. The cooling down of the resistor due to flow created by the breath is observed by a change in resistance.

When using a humidity sensor, one takes advantage of the presence of a different level of humidity in the breath compared to the environment.

The method to obtain the measure representative of the volume of gas using the breath sensing device according to the second embodiment is illustrated in FIG. 7.

In Step 101, the signal analyzing means 63 of the breath sensing device 91 receives the signals from the first and second breath sensing means 83 and 85. The signals received are analog or digital and can already be treated by applying filters etc.

In Step 103, the signal analyzing means 63 determines the difference between the signal received from the first and from the second breath sensing means 83, 85.

Furthermore, as illustrated in Step 105, by integrating the difference in the signals over the duration of the breath, one gets a measure that is proportional to the gas volume V that passed through the breath sensing device 21, just like in the first embodiment.

In the second embodiment, the beginning $t_0$ of the breath is the moment at which the difference between the signals received from the first and the second breath sensing means exceeds a predetermined first threshold. The end $t_1$ of the breath can be triggered by the subsequent point in time at which the difference falls below a second threshold, in particular the first threshold. According to a variant the end of the time frame could also be the moment at which the integral of the difference of the signals exceeds a third threshold.

The integration of the signal from the gas sensing means 43 is realized the same way as in the first embodiment. Furthermore, the calibration of the breath sensing device 91 of the second embodiment can be achieved just in the same manner as described above with respect to the first embodiment, that is for instance by comparing the ratio of the integrals with the value of the ratio as determined by a practitioner using a different method.

FIG. 8 illustrates schematically the third embodiment of the breath sensing device 121 according to the invention, in particular in relation to claim 3 or 4. Features with reference numerals already used in the description of the FIGS. 1 to 7 will not be described again but reference is made to their description above.

The breath sensing device according to the third embodiment comprises in addition to the acoustic wave sensing means 23, here the microphone, and the first gas sensing means 43 sensitive to at least one type of molecule, a second gas sensing means 123 sensitive to at least one other type of molecule, here in particular to $CO_2$.

Measuring the $CO_2$ has the advantage that it is directly related to the exhaled gas in the breath of a user. Whereas the concentration of $CO_2$ in ambient air is of the order of 0.04 percent by volume, this percentage is of the order of 3.5 to 5 percent by volume in the exhaled gas. Using a second gas sensing means 123 that is responsive to carbon dioxide, the important change, by about a factor 100 in $CO_2$ concentration can be exploited to identify the time period during which a user is blowing into the breath sensing device.

According to a variant of the third embodiment, the breath sensing device can comprise an humidity sensor in addition or as an alternative to the CO2 sensing means. In the case a humidity sensor is used, one also takes advantage of a parameter that is directly linked to the exhaled air in the breath of a user. Indeed, the amount of humidity of the exhaled gas of a user is typically different than the one of the environment. Thus, the signal coming from the humidity sensor will see a change in humidity when a user breaths into the sensing device.

FIG. 9 illustrates a method to determine a measure proportional to the volume of gas of a user's breath according to the third embodiment.

In Step 131, the signal analyzing means 63 of the breath sensing device 121 receives the signals from the second gas sensing means 123 or the humidity sensor and the signals from the first gas sensing means 43. The signals received are analog or digital and can already be treated by applying filters etc.

In Step 133, the signal analyzing means 63 integrates the signal received from the second gas sensing means 123 or the humidity sensor over the duration of the breath, so that a measure that is proportional to the gas volume V that passed through the breath sensing device 121, just like in the first and second embodiment.

In the third embodiment, the beginning $t_0$ of the breath is the moment at which the gas sensing means 123 detects a steep raise or a value larger than a first threshold, in the $CO_2$ signal, due to the difference of roughly a factor 100 between the $CO_2$ content in the ambient air and the $CO_2$ content in exhaled breath. The end $t_1$ of the breath can be triggered by the subsequent point in time at which the $CO_2$ falls below a second threshold, in particular the first threshold, or an important negative slope is observed in the signal. According to a variant the end of the time frame could also be the moment at which the integral of the signal of the $CO_2$ content exceeds a third threshold.

In step 135, the signal coming from the first gas sensing means 43 is integrated during the same time frame just like in the first and second embodiment.

The further calibration of the breath sensing device 121 of the third embodiment can be achieved just in the same manner as described above with respect to the first embodiment, that is for instance by comparing the ratio of the integrals with the value of the ratio as determined by a practitioner using a different method.

All previously discussed embodiments are not intended as limitations but serve as examples illustrating features and advantages of the invention. It is to be understood that some or all of the above described features can also be combined in different ways.

LIST OF REFERENCE NUMERALS 1 electronic device
3 housing
5 display device
7 sensing device
9 acoustic wave sensing means, microphone
11 gas sensing means
13 mother board
15 opening/hole
17 grid
21 sensing device
23 microphone
25 movable plate
27a,b pillar structure
29 substrate
31 fixed plate, stiff plate, back plate
33a-e perforations in the fixed plate
35 movement of the movable plate
37 air gap
39 ventilation path
41 air chamber
43 gas sensing means
45 gas sensitive layer
47a-e perforations 49 air or gas flow
51 sensing device's common housing
61 electronic device according to the first embodiment
63 signal analyzing means
71 step of receiving signal
73 step of determining the DC part of the signal
75 integrate DC signal
81 electronic device according to second embodiment
83 first breath sensing means
85 second breath sensing means
87 second hole in housing
89 second grid
91 part of a breath sensing device according to the second embodiment
101 receiving signals from first and second breath sensing means 83 and 85
103 determine difference between the two signals
105 integrate the difference over the time frame
121 breath sensing device according to the third embodiment
123 second gas sensing means or humidity sensor
131 receiving signal from second gas sensing means 123
133 integrating the signal received
135 integrating the signal from the first gas sensing means 43

The invention claimed is:

1. Breath sensing device for a portable telecommunication device, or a wearable device, the breath sensing device comprising:
an acoustic wave sensing means comprising a microphone, and
a first gas sensing means sensitive to at least one type of molecule and
a second gas sensing means sensitive to at least one other type of molecule,
wherein the acoustic wave sensing means is provided over a substrate and the first and second gas sensing means are stacked over the acoustic wave sensing means,
wherein one of the first and second gas sensing means is arranged over the remaining first and second gas sensing means, and
wherein perforations in the acoustic wave sensing means are respectively aligned with perforations in the first gas sensing means and perforations in the second gas sensing means along a thickness direction of the breath sensing device.

2. Method for sensing the breath of a human or an animal, using the breath sensing device according to claim 1, comprising the steps of:
starting integrating the signal received from the first gas sensing means over a predetermined time frame when the signal from the second gas sensing means a first threshold; and
starting integrating the signal received from the second gas sensing means over the predetermined time frame when the signal from the second gas sensing means or when the signal from the humidity sensor exceeds the first threshold to determine a signal proportional to the gas volume of the breath.

3. The method according to claim 2, wherein the end of the time frame is triggered by the subsequent point of time at which the difference of the signals or the signal from the second gas sensing means or the DC electrical signal contribution falls below a predetermined second threshold, wherein the predetermined second threshold is below the first threshold, or when the integral of the difference or the signal from the second gas sensing means or when the integral of the DC electrical signal contribution exceeds a third threshold.

4. The method according to claim 3, further comprising a step of determining a ratio based on the signal received from the gas sensing means and the signal proportional to the gas volume and calibrating the ratio using a value representative for the ratio obtained by a different sensing method.

5. Breath sensing device for a portable telecommunication device or a wearable device, the breath sensing device comprising:
an acoustic wave sensing means comprising a microphone with a membrane,
the microphone comprising a movable plate and a fixed plate, the fixed plate being arranged over the movable plate, so that the movable plate and the fixed plate form a capacitor,
the fixed plate comprising a plurality of holes;
a gas sensing means sensitive to at least one type of molecule,
the gas sensing means comprises a gas sensitive layer that is arranged over the fixed plate of the microphone,
the gas sensitive layer comprising a plurality of holes;
wherein the plurality of holes of the fixed plate of the microphone are respectively aligned with the plurality of holes of the gas sensitive layer of the gas sensing means along a thickness direction of the breath sensing device;
and further comprising a signal analyzing means configured to determine a DC electrical signal contribution to the total electrical signal received from the acoustic wave sensing means and configured to integrate the DC electrical signal over a predetermined time frame.

6. Breath sensing device according to claim 5, wherein the signal analyzing means is furthermore configured to integrate the electrical signal received from the gas sensing means over the predetermined time frame and to determine the ratio of the integrated electrical signal received from the gas sensing means and the integrated DC electrical signal.

7. The breath sensing device according to claim 5, wherein the gas sensing means is based on at least one of a metal oxide (MOX), carbon nanotubes (CNTs), a gold nanoparticle, a silicon nanowire, a quartz crystal microbalance (QCM), a colorimetric sensor, and a conductive polymer.

8. Method for sensing the breath of a human or an animal, using the breath sensing device according to claim 5, comprising the steps of:
determining a DC electrical signal contribution to the total electrical signal received from the acoustic wave sensing means; and
integrating the DC electrical signal over a predetermined time frame to determine a signal proportional to the gas volume of the breath.

9. The method according to claim 5, wherein the start of the time frame is triggered by the point in time at which a difference between the signals of the first and second breath sensing means or the DC electrical signal contribution exceeds a predetermined first threshold.

* * * * *